(12) United States Patent
Kim et al.

(10) Patent No.: US 12,104,069 B2
(45) Date of Patent: Oct. 1, 2024

(54) EPIDERMAL PENETRATION TYPE INK COMPOSITION

(71) Applicant: NATIONAL CANCER CENTER, Goyang-si (KR)

(72) Inventors: Seok-ki Kim, Goyang-si (KR); Sang Hyuk Lee, Daegu (KR); Jin Hee Noh, Goyang-si (KR)

(73) Assignee: NATIONAL CANCER CENTER, Goyang-si (KR)

(*) Notice: Subject to any disclaimer, the term of this patent is extended or adjusted under 35 U.S.C. 154(b) by 565 days.

(21) Appl. No.: 16/755,359

(22) PCT Filed: Oct. 1, 2018

(86) PCT No.: PCT/KR2018/011662
§ 371 (c)(1),
(2) Date: Apr. 10, 2020

(87) PCT Pub. No.: WO2019/074229
PCT Pub. Date: Apr. 18, 2019

(65) Prior Publication Data
US 2021/0139731 A1      May 13, 2021

(30) Foreign Application Priority Data

Oct. 11, 2017   (KR) .................. 10-2017-0131508

(51) Int. Cl.
| | | |
|---|---|---|
| *C09D 11/50* | (2014.01) | |
| *A61K 49/00* | (2006.01) | |
| *C09D 11/17* | (2014.01) | |
| *C09D 11/20* | (2006.01) | |

(52) U.S. Cl.
CPC .......... *C09D 11/50* (2013.01); *A61K 49/0023* (2013.01); *A61K 49/0028* (2013.01); *A61K 49/0032* (2013.01); *A61K 49/0034* (2013.01); *A61K 49/0054* (2013.01); *C09D 11/17* (2013.01); *C09D 11/20* (2013.01)

(58) Field of Classification Search
CPC .............. A61K 49/00; A61K 49/0023; A61K 49/0028; A61K 49/0032; A61K 49/0034; A61K 49/0054; C09D 11/50; C09D 11/17; C09D 11/20
USPC .................. 424/1.11, 1.65, 9.1, 9.6
See application file for complete search history.

(56) References Cited

U.S. PATENT DOCUMENTS

| | | | |
|---|---|---|---|
| 4,490,177 A | * | 12/1984 | Shioi ............... C09D 11/50 106/404 |
| 5,900,094 A | | 5/1999 | Santini et al. |
| 5,968,241 A | | 10/1999 | Santini et al. |
| 5,981,626 A | | 11/1999 | Santini et al. |
| 6,040,359 A | | 3/2000 | Santini et al. |
| 7,160,375 B2 | * | 1/2007 | Yamamoto ......... A61K 8/0262 106/490 |
| 7,208,018 B2 | | 4/2007 | Gourlaouen et al. |
| 9,333,795 B2 | * | 5/2016 | Fujii ................... B43K 1/082 |
| 9,439,848 B2 | | 9/2016 | Graham et al. |
| 9,724,288 B2 | | 8/2017 | Graham et al. |
| 10,166,302 B2 | | 1/2019 | Kim et al. |
| 2003/0060718 A1 | * | 3/2003 | Alam ................ A61K 41/0057 600/476 |
| 2005/0031562 A1 | | 2/2005 | Gourlaouen et al. |
| 2010/0056647 A1 | | 3/2010 | Graham et al. |
| 2014/0374671 A1 | | 12/2014 | Chopra et al. |
| 2015/0328345 A1 | | 11/2015 | Kim et al. |
| 2016/0338939 A1 | | 11/2016 | Graham et al. |

FOREIGN PATENT DOCUMENTS

| | | |
|---|---|---|
| JP | 3336403 B2 | 10/2002 |
| JP | 2006-249104 A | 9/2006 |
| JP | 2015-7231 A | 1/2015 |
| KR | 10-0338693 B1 | 5/2002 |
| KR | 10-2004-0060393 A | 7/2004 |
| KR | 10-2011-0067114 A | 6/2011 |
| KR | 10-2015-0042170 A | 4/2015 |

OTHER PUBLICATIONS

International Search Report issued on Jan. 24, 2019 in PCT/KR2018/011662 filed on Oct. 1, 2018, 3 pages.

\* cited by examiner

*Primary Examiner* — D. L. Jones
(74) *Attorney, Agent, or Firm* — Oblon, McClelland, Maier & Neustadt, L.L.P.

(57) ABSTRACT

The present invention provides an epidermal penetration type ink composition comprising: a fluorescent colorant containing at least one selected from the group consisting of indocyanine green (ICG), cyanine, phthalocyanine, oxazine, rhodamine, and a mixture thereof; a binder resin containing at least one of polyvinylpyrrolidone (PVP) and polyvinylbutyral (PVB); and a solvent containing at least one of ethanol and isopropanol.

4 Claims, 4 Drawing Sheets

EPIDERMAL PENETRATION TYPE INK COMPOSITION

CROSS-REFERENCE TO RELATED APPLICATION

This application claims priority to and the benefit of Korean Patent Application No. 10-2017-0131508, filed on Oct. 11, 2017, the disclosure of which is incorporated herein by reference in its entirety.

TECHNICAL FIELD

The present invention relates to an epidermal penetration type ink composition.

BACKGROUND ART

The content described in this section merely provides background information on the present invention and does not constitute the related art In the medical field, a line- or dot-shaped mark is drawn on a skin surface to correctly mark a surgical site before surgery, to mark anatomical structures important to diagnosis and treatment processes such as diagnostic imaging and the like, or to align the skin for skin suturing or the like. Currently, "medical in-vitro markers" such as pens and tattoos are widely used for such purposes. In the case of simple surgery, it is sufficient if the mark lasts for several minutes, while in the case of radiotherapy or the like, the mark needs to be maintained for several weeks. Since an ink applied to a skin surface is removed in a few days due to daily washing activities such as facial cleansing, showering, and the like, there is an inconvenience of having to reapply the ink once every few days (approximately every two to three days). In situations where the ink cannot be reapplied every few days, it may be difficult for the patient to continue his or her daily routine such as facial cleansing, showering, or the like for several weeks.

DISCLOSURE

Technical Problem

A related art relating to a penetrating ink composition (Korean Patent Publication No. 10-2004-0060393) discloses an ink composition which allows a printed pattern of the penetrating ink applied to an object such as paper or fabric to appear on the backside of the object. Although this ink composition may offer the advantage of preventing the falsification of security documents, important documents, and the like, it may be unreasonable to apply the same to the human body for medical use.

Therefore, the present invention is directed to providing an epidermal penetration type ink composition in which the above-described disadvantages of the prior art have been remedied, that is, an epidermal penetration type ink composition which is applicable to the human body and provides a mark that lasts for an extended period of time without being removed.

Technical Solution

One aspect of the present invention provides an epidermal penetration type ink composition which includes: a fluorescent colorant including at least one selected from the group consisting of indocyanine green (ICG), cyanine, phthalocyanine, oxazine, rhodamine, and a mixture thereof; a binder resin including at least one of polyvinylpyrrolidone (PVP) and polyvinyl butyral (PVB); and a solvent including at least one of ethanol and isopropanol.

Other aspects of the present invention will be described in part in the description that follows, and may be readily identifiable in part from the description or learned by the practice of the present invention.

Both the foregoing general description and the following detailed description are merely illustrative and exemplary and do not limit the present invention described in the claims.

Advantageous Effects

The epidermal penetration type ink composition of the present invention exhibits an excellent cosmetic effect in that fluorescence is not visually discernible and is generated and easily identified only when irradiated with near-infrared rays.

The epidermal penetration type ink composition of the present invention can be absorbed into the epidermal layer of the human body and more specifically into the stratum corneum of the skin arid thus can provide a mark that lasts for an extended period of time.

The epidermal penetration type ink composition of the present invention contains a pigment with relatively low human toxicity and thus can be applied to the human body without much risk.

NODES OF THE INVENTION

Figure 1:
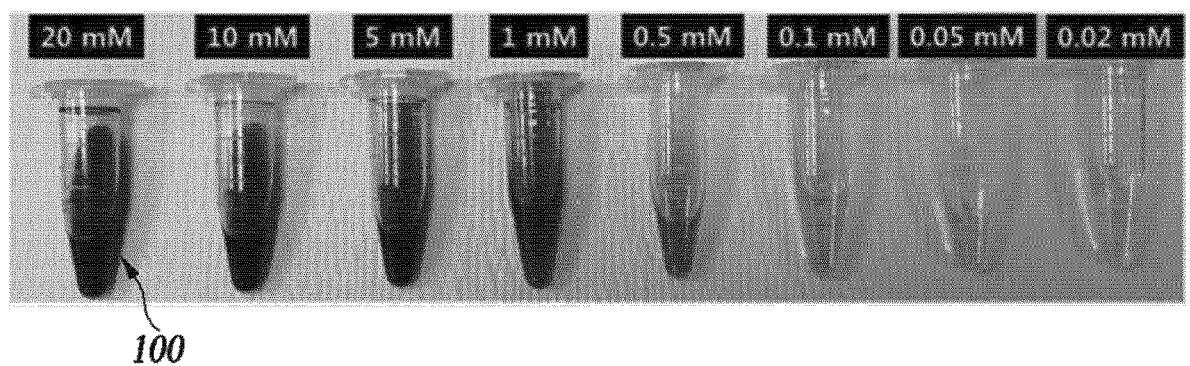
FIG. 1 shows a set of samples prepared for an experiment on application concentrations of a fluorescent colorant of an epidermal penetration type ink composition according to one embodiment of the present invention and listed by concentration.

Hereinafter, specific embodiments of the present invention will be described in detail with reference to the accompanying drawings.

However, in describing the specific embodiments of the present invention, when it is determined that a detailed description of a known function or configuration related to the present invention may unnecessarily obscure the gist of the present invention, the detailed description may be omitted.

An epidermal penetration type ink composition 100 of the present invention may include a fluorescent colorant 200, a binder resin, and a solvent.

The fluorescent colorant 200 is a fluorescent pigment that is normally not visually discernible but generates fluorescence only when irradiated with near-infrared rays to be visually detected. The fluorescent colorant 200 may include at least one selected from the group consisting of indocyanine green (ICG), cyanine, phthalocyanine, oxazine, rhodamine, and a mixture thereof, As the fluorescent colorant, a near-infrared fluorescent pigment and specifically a near-infrared fluorescent pigment that is harmless to the human body may be used so that the fluorescent colorant is applicable to the human body. The above-described ICG, cyanine, phthalocyanine, oxazine, and rhodamine can generate fluorescence in the near-infrared region and are suitable for an application to the human body. Any one of the above may be selected and used as the fluorescent colorant, but the present invention is not limited thereto, and alternatively, any mixture thereof may be used as the fluorescent colorant.

However, the materials that may be included in the fluorescent colorant are not limited to those described above, and any known material may be used as long as it can play the role of a fluorescent colorant well.

The binder resin is mixed with the fluorescent colorant to impart suitable viscosity to the ink so that the ink can settle on an object to be marked without flowing down. In addition, after the solvent is volatilized, the binder resin may allow the fluorescent colorant to be bound to the object to be marked.

The viscosity of the ink composition varies depending on the concentration of the hinder resin, and typically the viscosity of the ink may be in the range of 300 to 25,000 cps.

The binder resin may include at least one selected from the group consisting of polyvinylpyrrolidone (PVP), polyvinyl butyral (PVB), and a mixture thereof.

The solvent may dissolve the fluorescent colorant 200 and the binder resin, whereby the penetrability of the fluorescent colorant can be improved and the fluorescent colorant can generate stable and long-lasting fluorescence. The solvent may include a main solvent and an auxiliary solvent. The main solvent may include at least one selected from the group consisting of 2-phenoxyethanol and benzyl alcohol, which have a high boiling point, and a mixture thereof. The auxiliary solvent may be propylene glycol methyl ether, which has a low boiling point. In addition, as an additional auxiliary solvent, at least one selected from the group consisting of ethanol (EtOH), isopropanol, and a mixture thereof may be further used.

However, the materials that may be included in the solvent are not limited to those described above, and any known material may be used as long as it can play the role of a solvent well.

FIG. 1 shows a set of samples prepared for an experiment on application concentrations of a fluorescent colorant of an epidermal penetration type ink composition according to one embodiment of the present invention arid listed by concentration.

Figure 2:
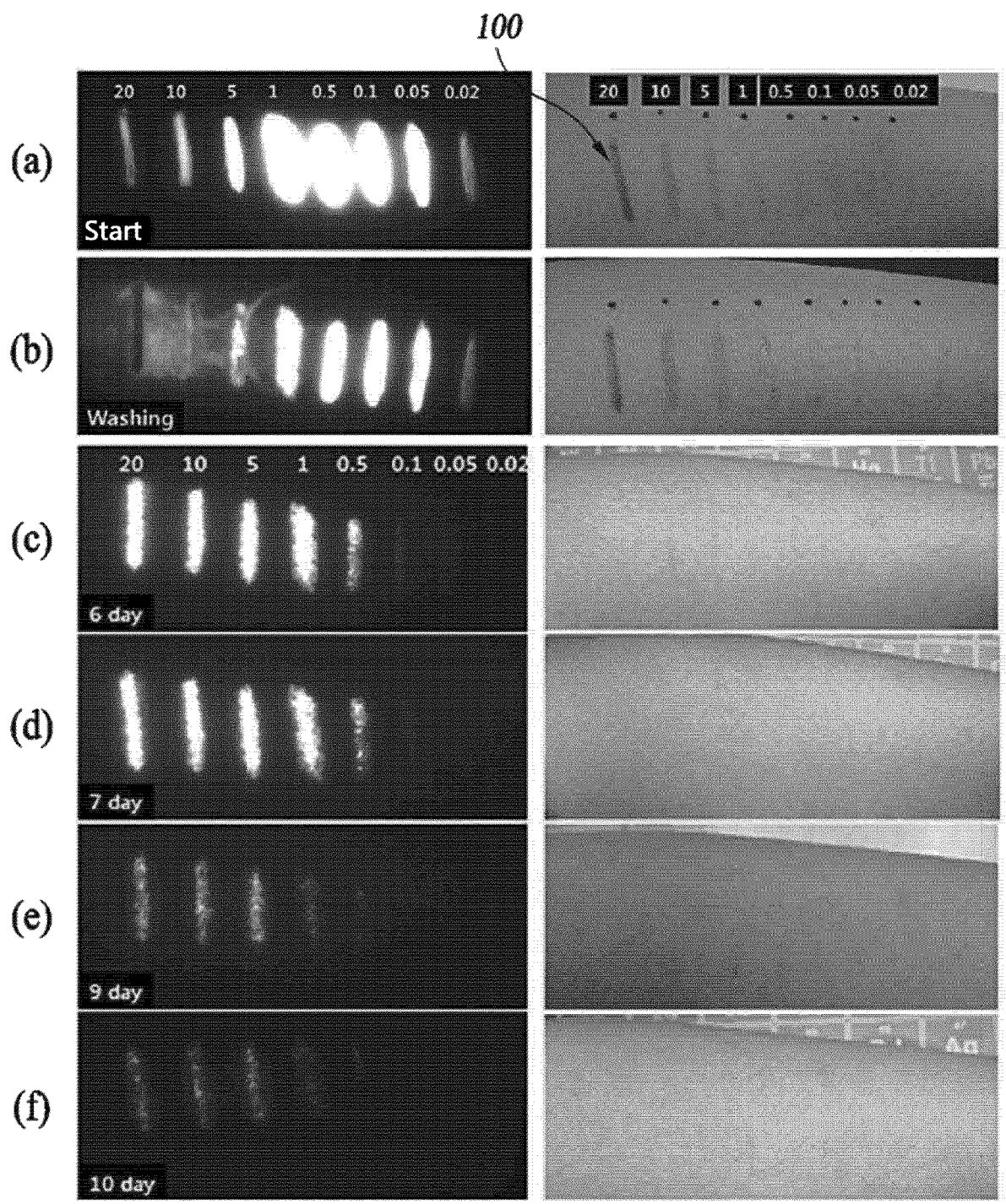
FIG. 2 shows experimental data by which the duration of light emission per concentration of an epidermal penetration type ink composition according to one embodiment of the present invention is graspable.

FIG. 2 shows experimental data by which the duration of light emission per concentration of an epidermal penetration type ink composition according to one embodiment of the present invention is graspable.

Referring to FIGS. 1 and 2, the result of an experiment in which an epidermal penetration type ink composition 100 according to one embodiment of the present invention was applied to a skin surface of the human body while varying the concentration of the fluorescent colorant 200 contained in the ink composition 100 frog 0.02 mM to 20 mM can be grasped. Here, ICG was adopted as the fluorescent colorant 200 of the ink composition 100, and the experiment was carried out while the concentrations of constituents except the ICG were fixed.

Referring to (a) to (f) of FIG. 2, it can be seen from the results of a 10-day experiment that fluorescence was observed when the concentration of the fluorescent colorant 200 was in the range of 0.02 mM to 20 mM, Referring to (c) to (f) in FIG. 2 it can be seen that from day 6 after the ink composition 100 was applied to the epidermis, the ink composition 100 which was not visually discernible emitted fluorescence when irradiated with near-infrared light. Referring to (a) and (b) of FIG. 2, it can be seen that immediately after the ink composition 100 was applied to the epidermis and immediately after washing was performed, the intensity of fluorescence was strongest when the concentration of the fluorescent colorant 200 was in the range of 0.05 mM to 5 mM.

However, it can be seen from the results of the 10-day experiment that the fluorescence was longest lasting and the intensity thereof was highest when the concentration of the fluorescent colorant 200 was in the range of 1 mM to 5 mM. Here, 1 mM may be the most preferable considering the degree of coloring that can be visually recognized, the amount of the fluorescent colorant 200, the duration of fluorescence, the intensity of fluorescence, and the like. However, the concentration is not necessarily limited thereto and may be in the range of 0.5 mM to 1.5 mM.

Figure 3:
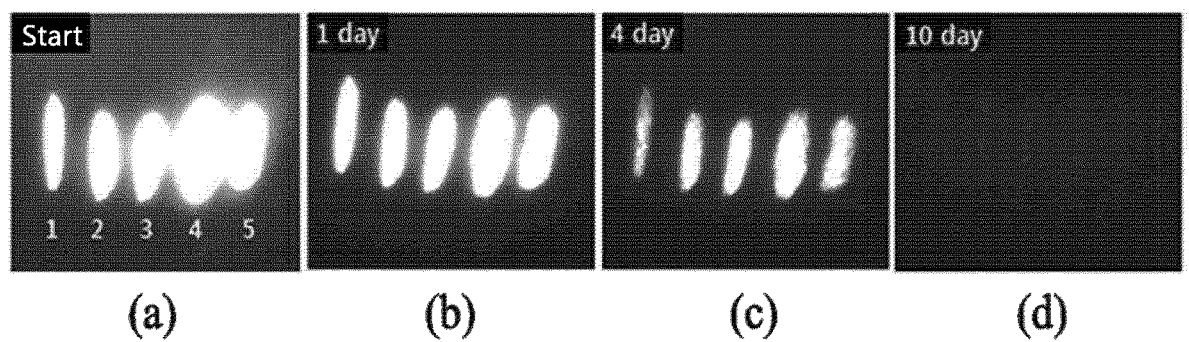
FIG. 3 shows experimental data by which the duration of light emission per solvent content of an epidermal penetration type ink composition according to one embodiment of the present invention is graspable.

FIG. 3 shows experimental data by which the duration of light emission per solvent content of an epidermal penetration type ink composition according to one embodiment of the present invention is graspable.

Referring to FIG. 3, it is possible to grasp the degree of fluorescence generation and the duration of fluorescence generation per ethanol content when ethanol is included as an additional auxiliary solvent.

Specifically, FIG. 3 illustrates an experimental example in which ethanol was included as an auxiliary solvent in the ink composition 100, where the degree of fluorescence generation and the duration of fluorescence generation according to the ratio of ethanol and the rest of the ink composition solution excluding ethanol were measured.

The numbers 1 to 5 shown in FIG. 3 are serial numbers that have been assigned according to content ratios of the rest of the solution to ethanol, and the content ratios can be seen in the following table.

TABLE 1

| | Rest of solution (mL) | EtOH (mL) |
|---|---|---|
| 1 | 1 | 0 |
| 2 | 0.95 | 0.05 |
| 3 | 0.9 | 0.1 |
| 4 | 0.8 | 0.2 |
| 5 | 0.7 | 0.3 |

As can be seen from the experimental results, on day 10 after the ink composition was applied to the epidermis (shown in (d) of FIG. 3), fluorescence was observed when the ratio of the rest of the solution to ethanol was #2 (0.95:0.05), #3 (0.9:0.1), and #4 (0.8:0.2). In the case of #5 (0.7:0.3), it was difficult to clearly identify the fluorescence as the proportion of ethanol became 0.3 or more. That is, it was found that the proportion of ethanol being 5 to 20 wt % relative to the total of 100 wt % was advantageous in terms of the degree of fluorescence generation and the duration of fluorescence generation. Particularly, it was observed that the degree of fluorescence generation on day 10 was highest when the proportion of ethanol was in the range of 5 to 10 wt % relative to the total of 100 wt %.

Figure 4:
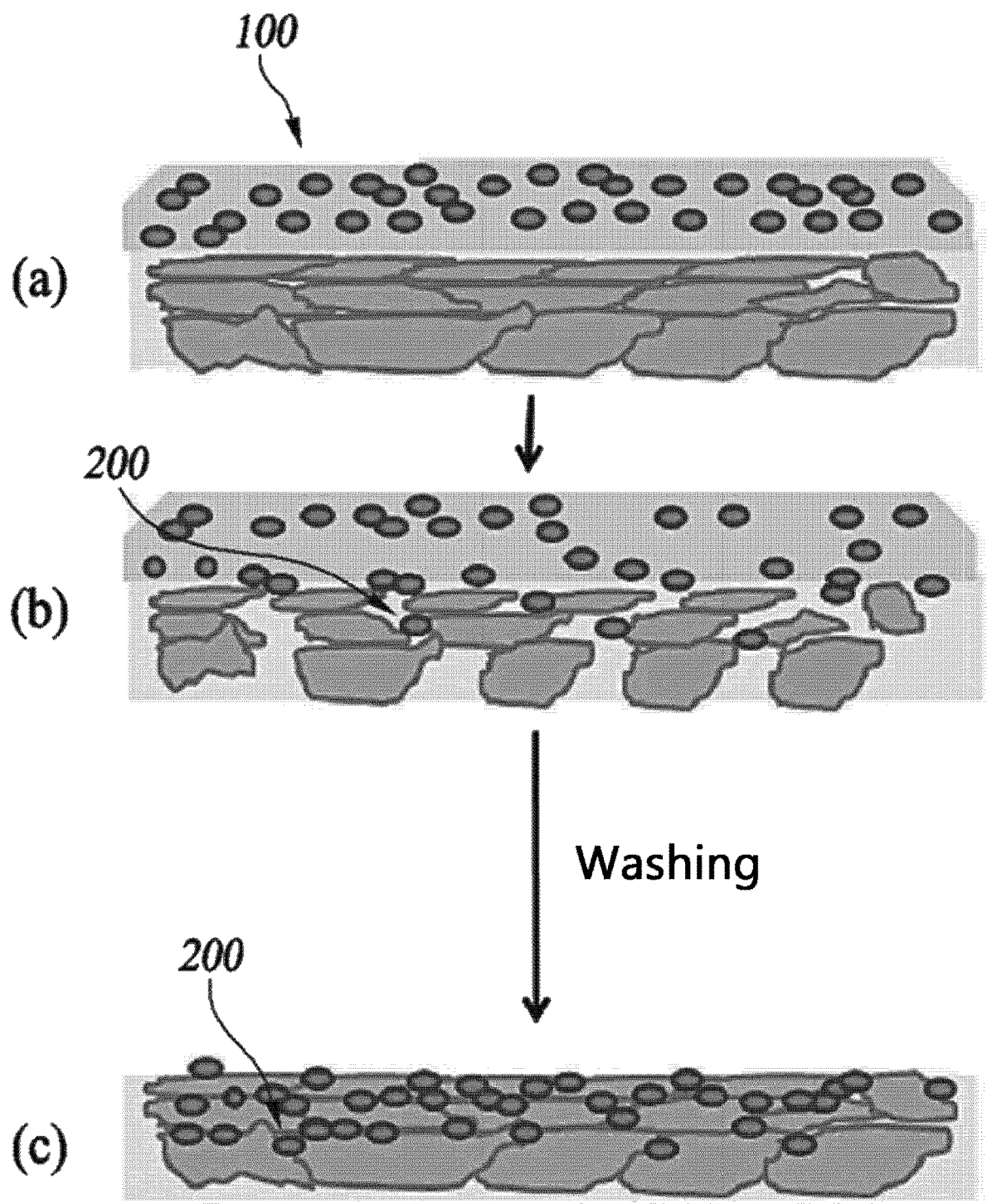
FIG. 4 is a conceptual diagram illustrating processes in which an epidermal penetration type ink composition according to one embodiment of the present invention penetrates and remains in the epidermis.

FIG. 4 is a conceptual diagram illustrating processes in which an epidermal penetration type ink composition according to one embodiment of the present invention penetrates and remains in the epidermis.

Referring to (a) of FIG. 4, it illustrates the application of the ink composition 100 to an object to be marked, that is, for example, the human skin. Referring to (b) of FIG. 4, when a few seconds to a few minutes have passed after application, the barrier of the stratum of the human skin may be temporarily weakened so that the composition can easily penetrate into the skin, and the fluorescent colorant 200 is allowed to penetrate through the barrier. Referring to (c) of FIG. 4, once the fluorescent colorant 200 has penetrated through the weakened barrier of the stratum corneum, it may not be possible to remove the fluorescent colorant even by washing the affected area.

The above-described solvent may be used as a skin permeation-promoting agent, and as can be seen from the foregoing description of (b) of FIG. 4, the solvent can promote the penetration of the composition into the skin epidermal layer by dissolving the stratum corneum of the skin surface.

It should be understood that the above-described embodiment is merely illustrative of the technical spirit of the present invention and that those skilled in the art to which the present invention pertains will be able to make various modifications and variations of this embodiment without departing from essential characteristics of the present invention. The embodiment is merely presented by way of example and is not intended to limit the technical spirit of the present invention, and therefore, the scope of rights of the present invention is not limited by the embodiment. The scope of protection of the present invention should be interpreted based on the claims, and all technical concepts which are acknowledged to be the same or equivalent to the scope of protection of the present invention should be interpreted as being included in the scope of rights of the present invention.

The invention claimed is:

1. An ink composition which penetrates into the stratum corneum of the skin, comprising:
    a fluorescent colorant, wherein the fluorescent colorant is indocyanine green (ICG);
    a binder resin, wherein the binder resin is a combination of polyvinylpyrrolidone (PVP) and polyvinyl butyral (PVB); and
    a solvent, wherein the solvent is ethanol,
    wherein a concentration of fluorescent colorant is in the range of 0.02 mM to 20 mM, a concentration of the combination of PVP and PVB is the range of 3 to 5 wt % relative to the total composition of 100 wt %, and an amount of the ethanol is in the range of 5 to 10 wt % relative to the total composition of 100 wt %.

2. The ink composition of claim 1, wherein the concentration of the ICG is in the range of 1 mM to 5 mM.

3. The ink composition of claim 1, wherein amounts of the PVP and the PVB are in the range of 0.9 to 1.8 wt % and 2.7 to 3.6 wt %, respectively, relative to the total composition of 100 wt %.

4. The ink composition of claim 1, further comprising an additional solvent, which is isopropanol.

* * * * *